United States Patent
Kobayashi et al.

(10) Patent No.: US 11,395,600 B2
(45) Date of Patent: Jul. 26, 2022

(54) VIBRATION WAVEFORM SENSOR AND PULSE WAVE DETECTION DEVICE

(71) Applicant: TAIYO YUDEN CO., LTD., Tokyo (JP)

(72) Inventors: Keiichi Kobayashi, Takasaki (JP); Takashi Ishiguro, Takasaki (JP)

(73) Assignee: TAIYO YUDEN CO., LTD., Tokyo (JP)

( * ) Notice: Subject to any disclaimer, the term of this patent is extended or adjusted under 35 U.S.C. 154(b) by 941 days.

(21) Appl. No.: 16/096,076

(22) PCT Filed: Feb. 9, 2017

(86) PCT No.: PCT/JP2017/004690
§ 371 (c)(1),
(2) Date: Oct. 24, 2018

(87) PCT Pub. No.: WO2017/187710
PCT Pub. Date: Nov. 2, 2017

(65) Prior Publication Data
US 2019/0133463 A1    May 9, 2019

(30) Foreign Application Priority Data

Apr. 28, 2016  (JP) .............................. JP2016-090079
Aug. 16, 2016  (JP) .............................. JP2016-159758
Nov. 18, 2016  (JP) .............................. JP2016-225514

(51) Int. Cl.
*A61B 5/0245*   (2006.01)
*B06B 1/06*     (2006.01)
(Continued)

(52) U.S. Cl.
CPC .......... *A61B 5/0245* (2013.01); *A61B 5/0265* (2013.01); *A61B 5/02444* (2013.01);
(Continued)

(58) Field of Classification Search
CPC . A61B 5/0245; A61B 5/02444; A61B 5/0265; A61B 5/6826; B06B 1/06; G01H 11/08
See application file for complete search history.

(56) References Cited

U.S. PATENT DOCUMENTS 3,792,204 A * 2/1974 Murayama ............. H01G 7/023
                                                     310/340
4,607,145 A * 8/1986 Ravinet .................. H04R 1/04
                                                     381/190
(Continued)

FOREIGN PATENT DOCUMENTS

EP     2881035 A4 *  4/2016  ........... A61B 5/6826
JP     S5234592 U    3/1977
(Continued)

OTHER PUBLICATIONS

International Search Report (ISR) dated Apr. 4, 2017, issued for International application No. PCT/JP2017/004690.

*Primary Examiner* — Navin Natnithithadha
(74) *Attorney, Agent, or Firm* — Law Office of Katsuhiro Arai

(57) ABSTRACT

In an exemplary embodiment, a vibration waveform sensor includes a pair of conductive pads 22, 23, and a piezoelectric element 30 whose terminal electrodes are connected thereto, which are provided on a board 20, and these are surrounded by a conductive ring-like spacer 40. On the interior side of the spacer 40, a cover part 44 substantially like a disk is provided in a manner covering over the pair of conductive pads 22, 23 and the piezoelectric element 30. The cover part 44 cuts off any humming noise from the top face of the piezoelectric element 30 over a continuous surface, which results in a reduction of humming noise.

19 Claims, 11 Drawing Sheets

(51) Int. Cl.
*G01H 11/08* (2006.01)
*A61B 5/024* (2006.01)
*A61B 5/0265* (2006.01)
*A61B 5/00* (2006.01)

(52) U.S. Cl.
CPC ............... *B06B 1/06* (2013.01); *G01H 11/08* (2013.01); *A61B 5/6826* (2013.01)

(56) References Cited

U.S. PATENT DOCUMENTS

| | | | | |
|---|---|---|---|---|
| 4,692,942 | A * | 9/1987 | Morgand | ................ H04R 7/22 |
| | | | | 381/114 |
| 2011/0288436 | A1 | 11/2011 | Stone | |
| 2015/0141774 | A1* | 5/2015 | Ogawa | ................... A61B 5/349 |
| | | | | 600/301 |

FOREIGN PATENT DOCUMENTS

| | | | |
|---|---|---|---|
| JP | S5234593 U | 3/1977 | |
| JP | H03186247 A | 8/1991 | |
| JP | 2003153389 A | 5/2003 | |
| JP | WO2010024417 A1 | 1/2012 | |
| JP | 2014042579 A | 3/2014 | |
| JP | 2015025769 A | 2/2015 | |
| WO | 2010024417 A1 | 3/2010 | |
| WO | WO-2014021335 A1 * | 2/2014 | ............... A61B 5/08 |

* cited by examiner

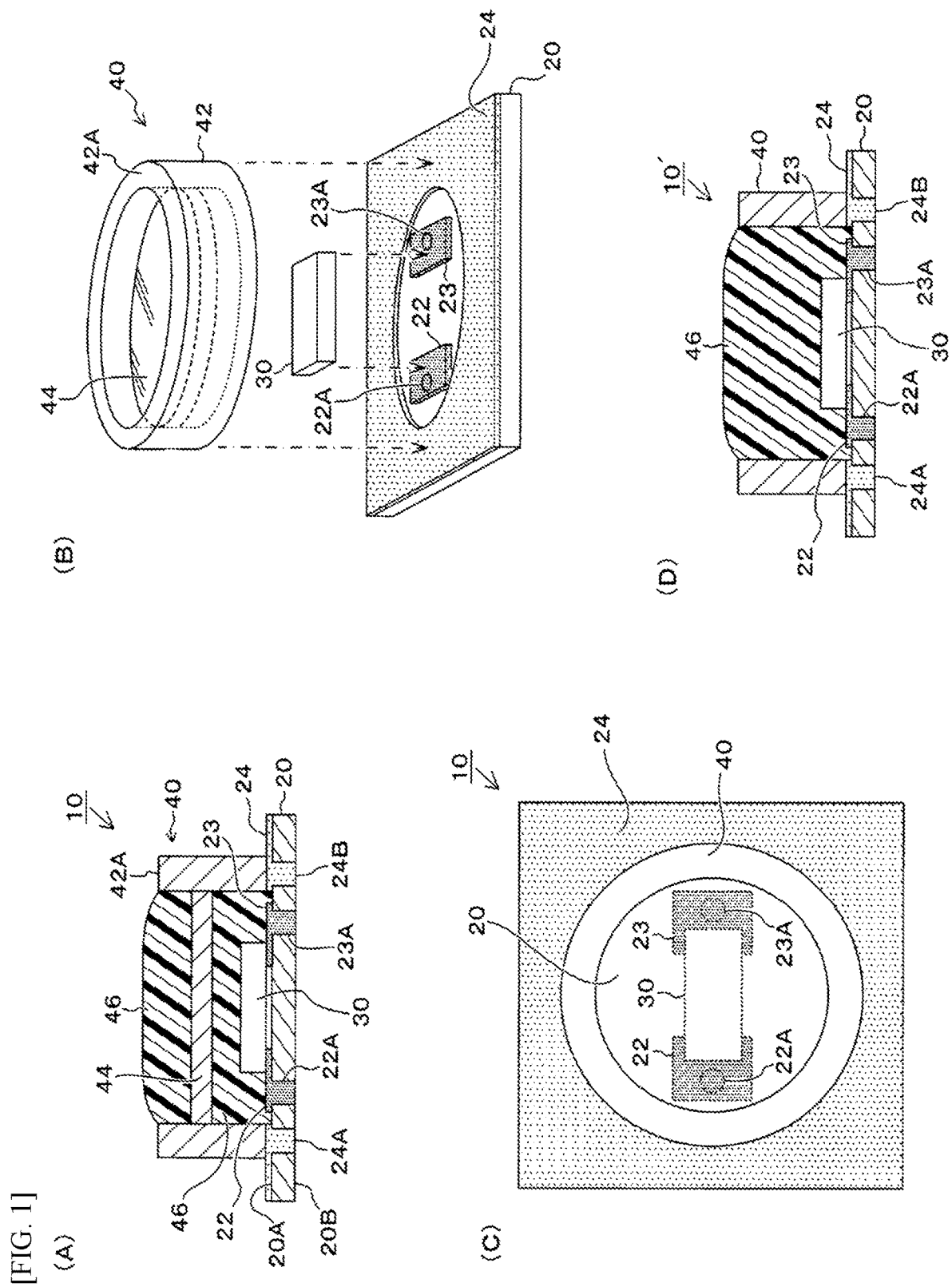
[FIG. 1]

[FIG. 2]
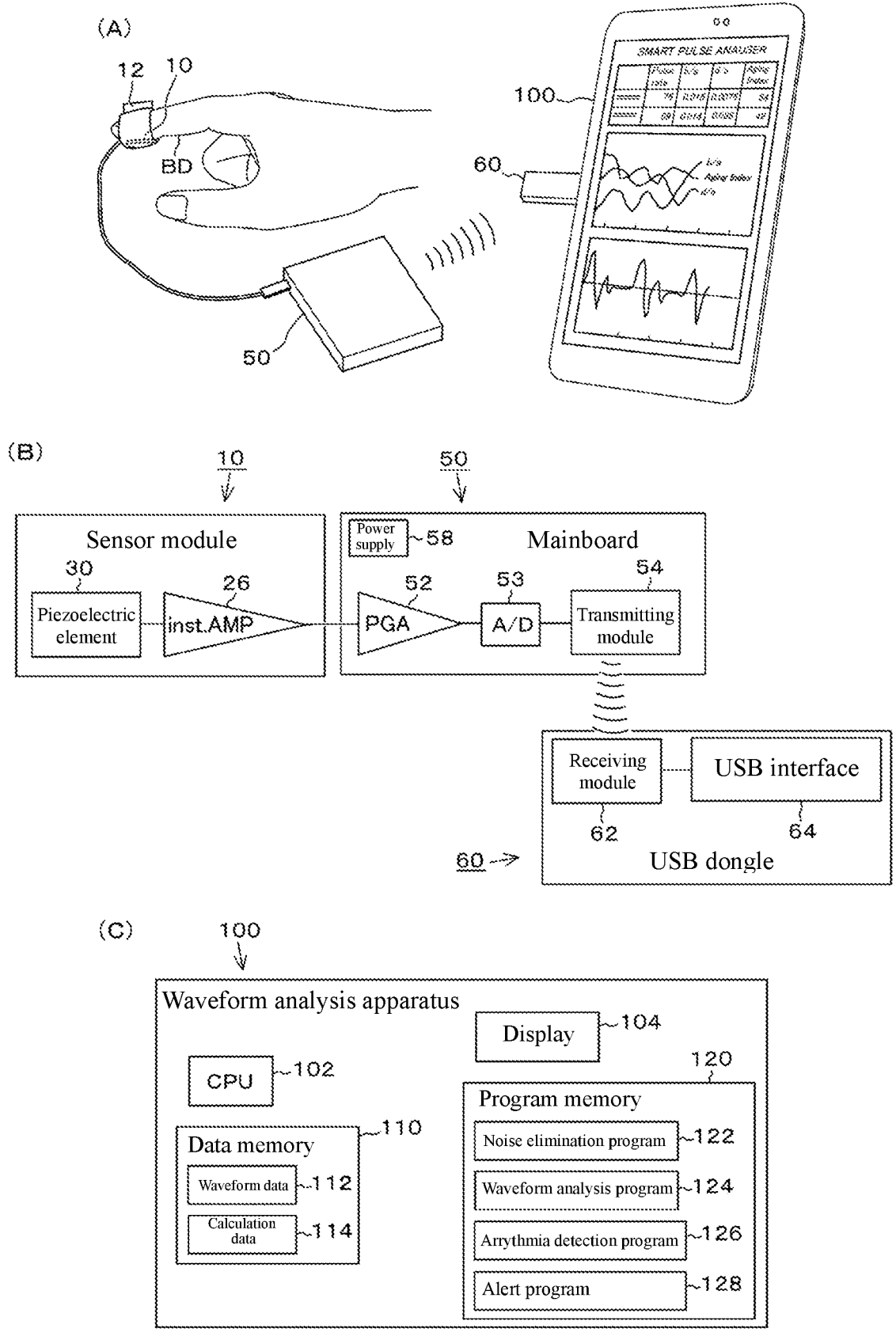

[FIG. 3]
(A)
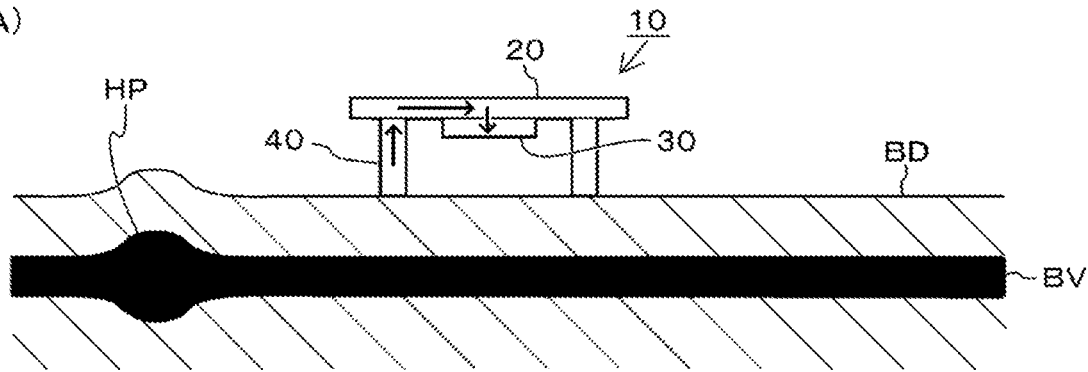
(B)
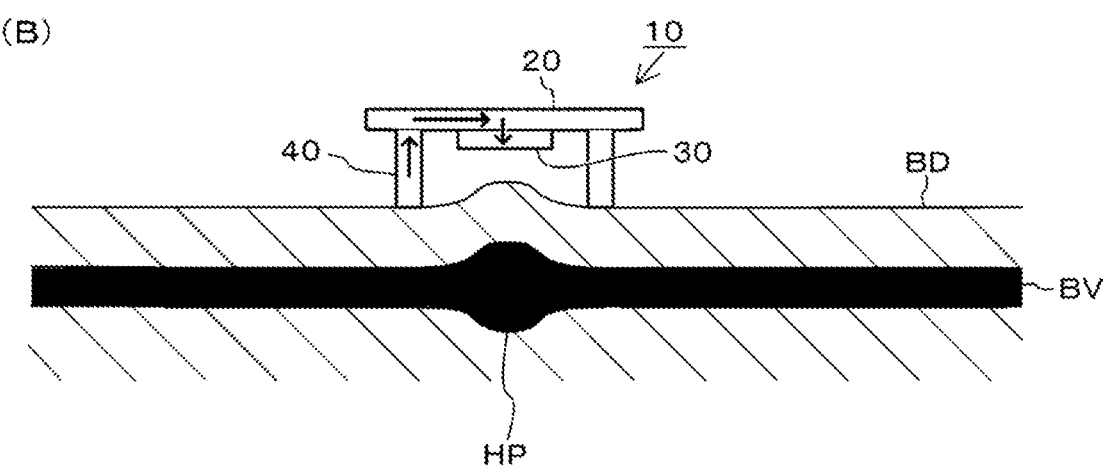
(C)
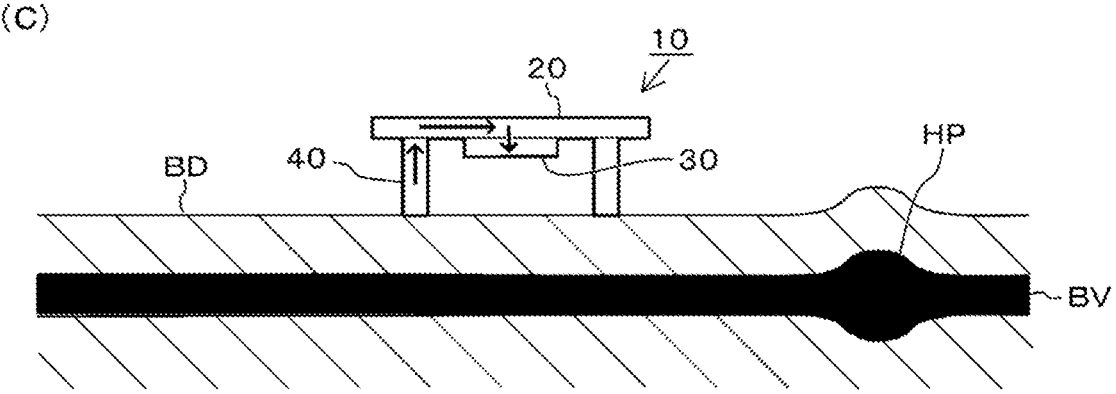

[FIG. 4]
(A)
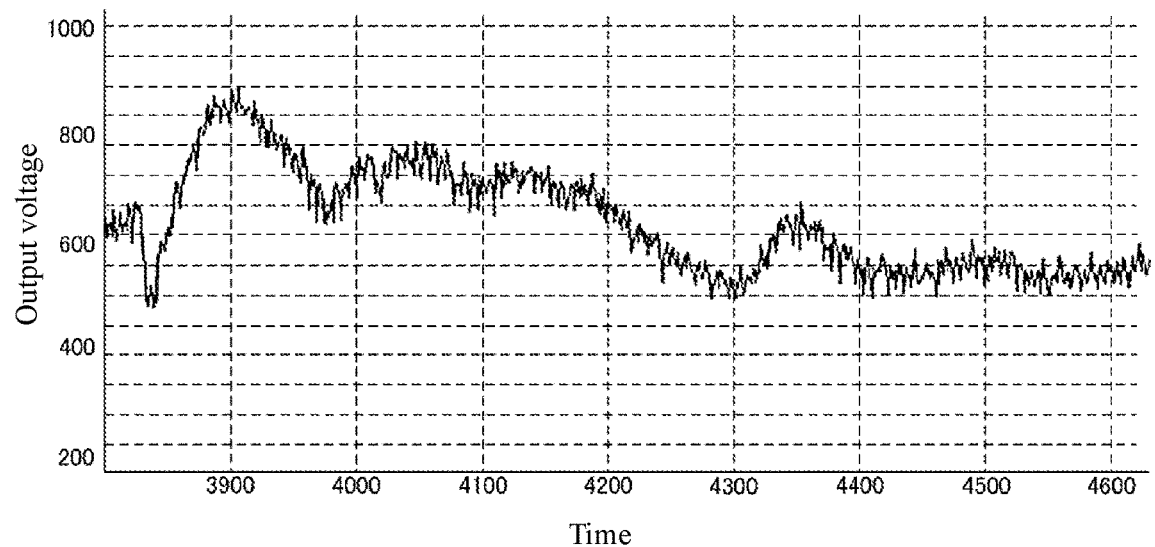
(B)
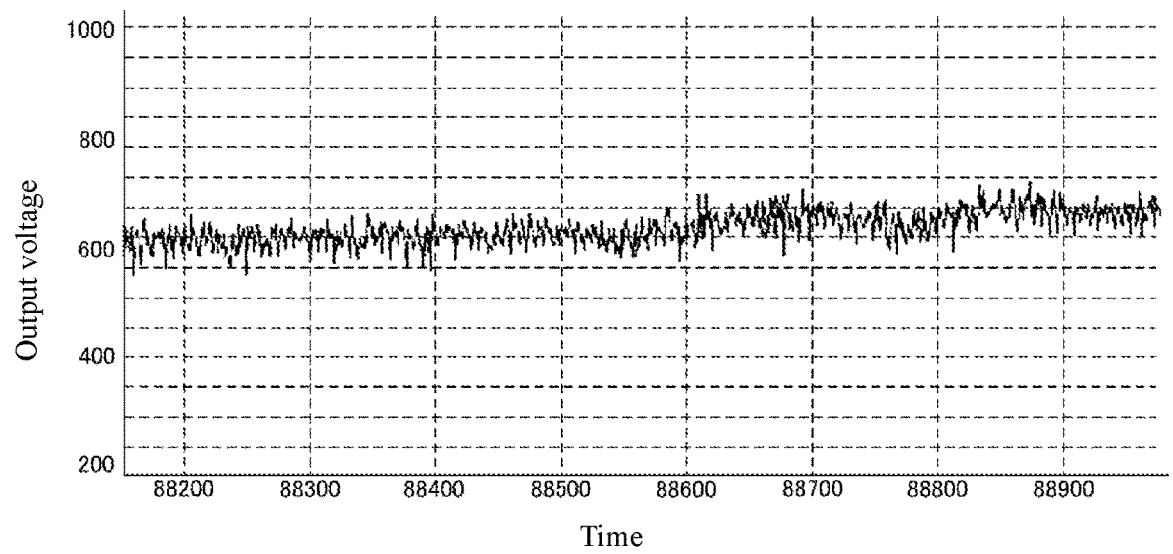

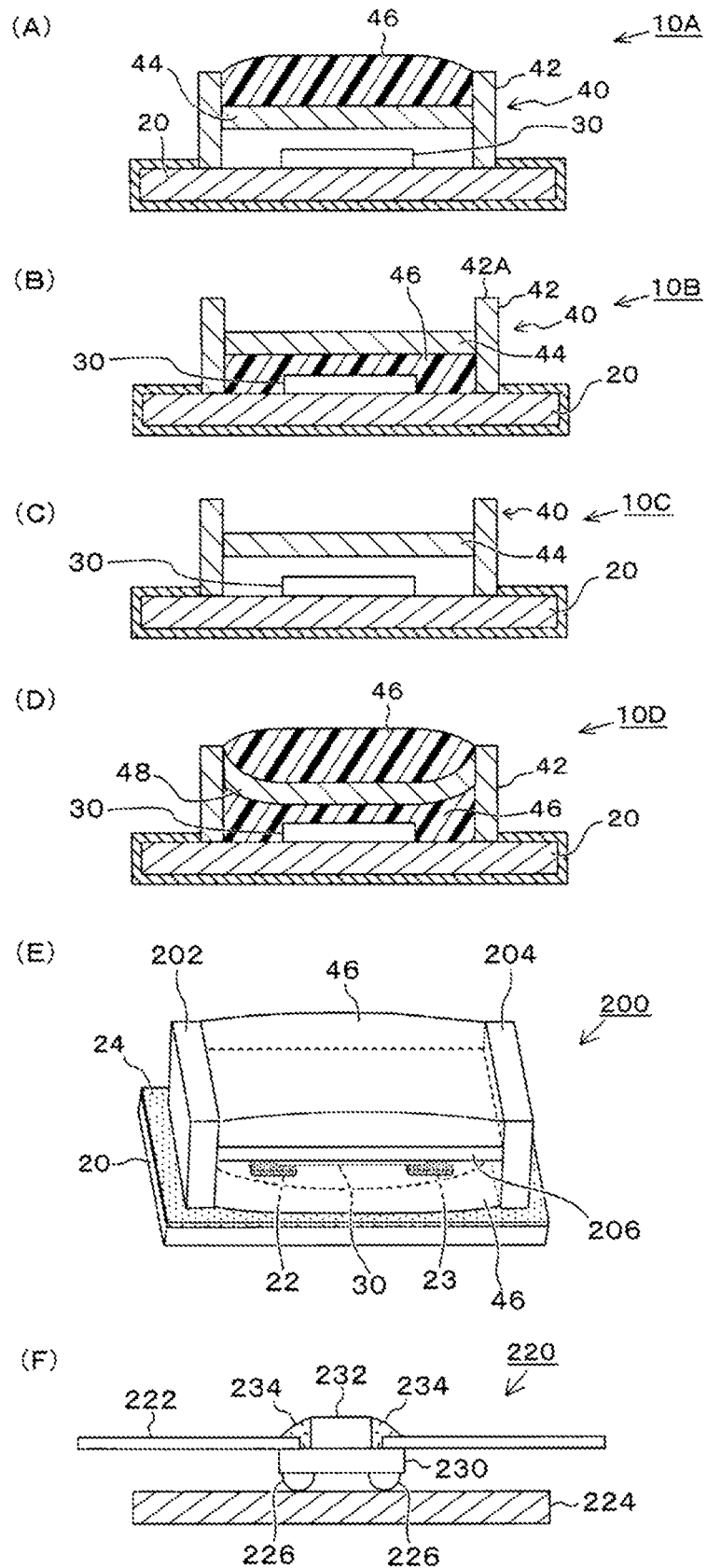
[FIG. 5]

[FIG. 6]
(A)
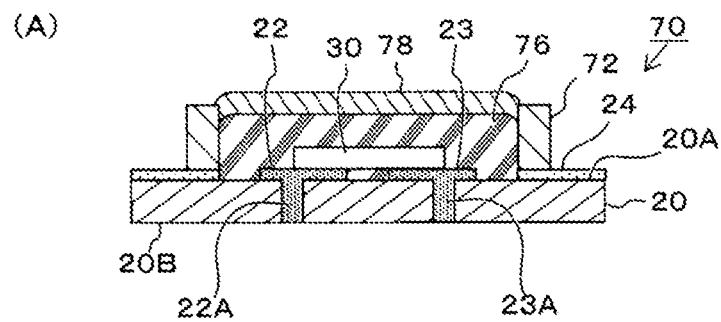
(B)
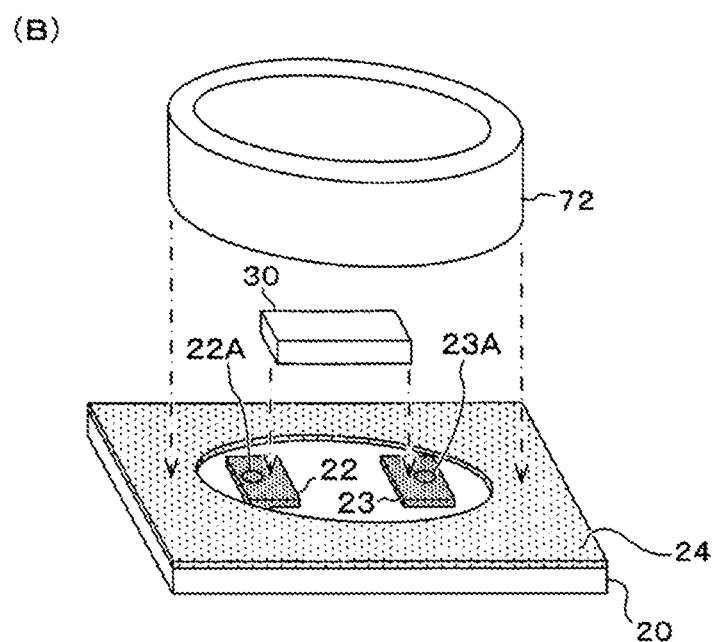
(C)
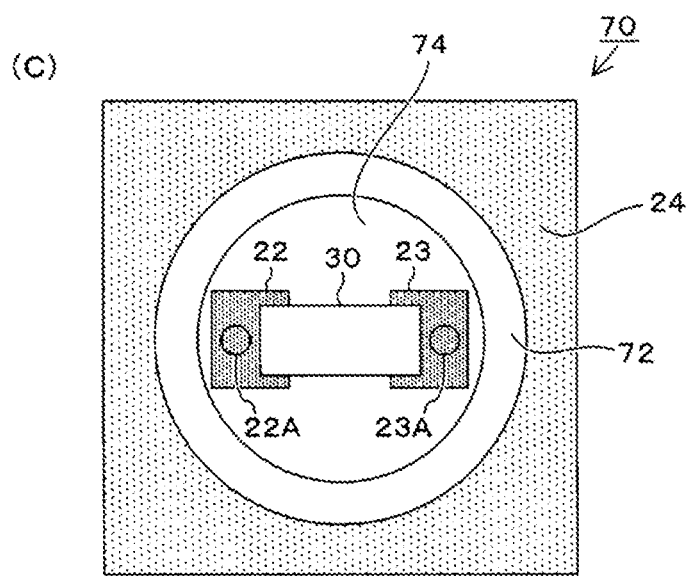

[FIG. 7]
(A)
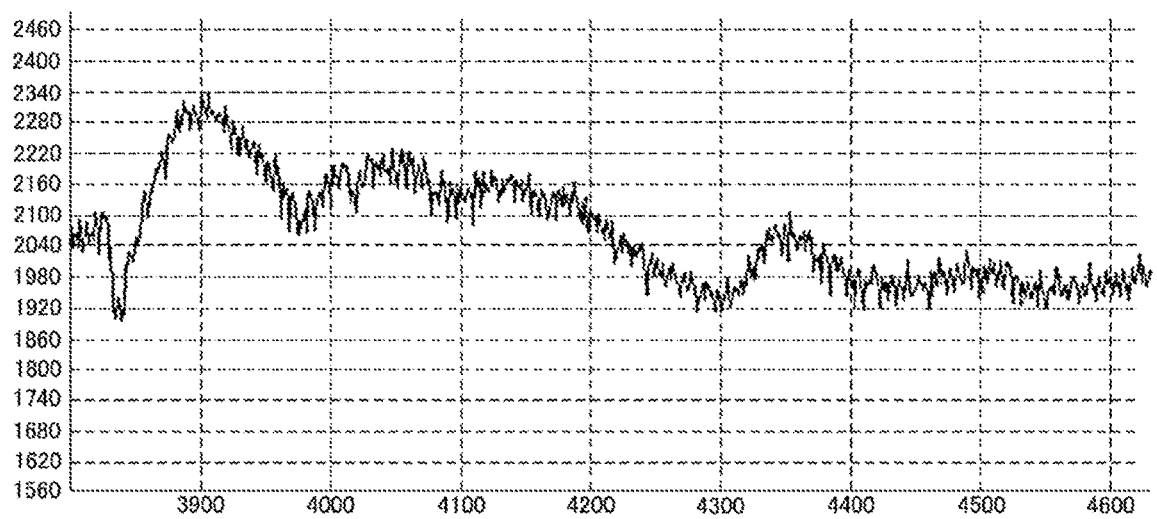
(B)
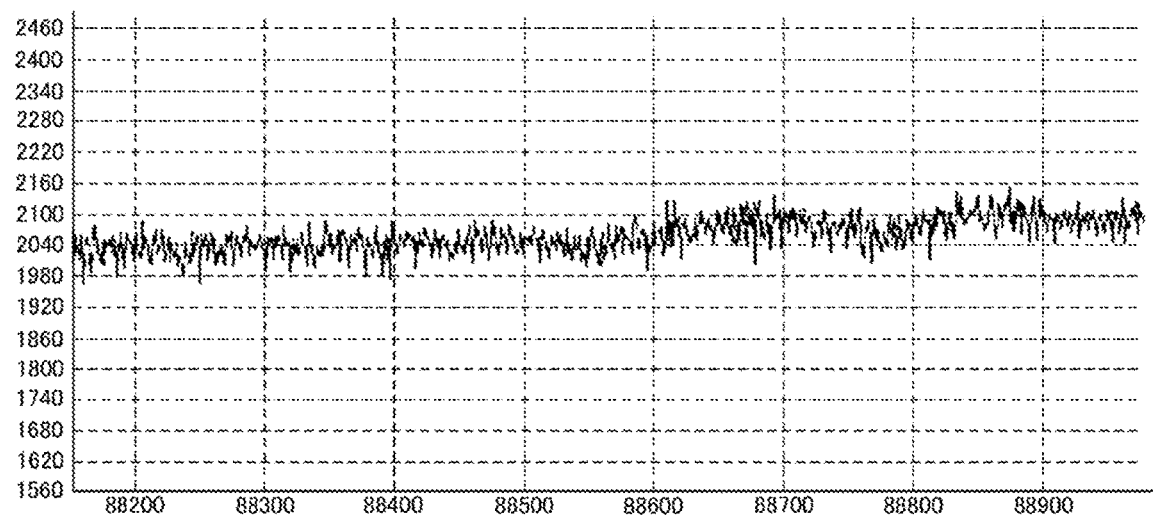

[FIG. 8]
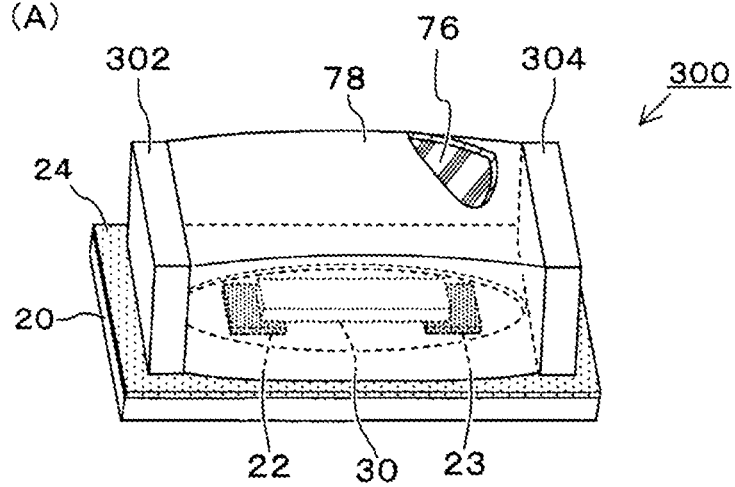
(A)
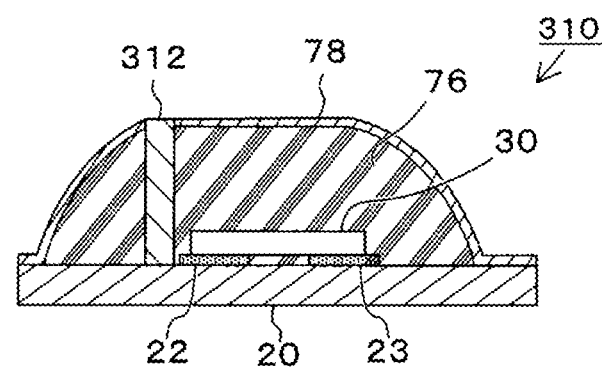
(B)
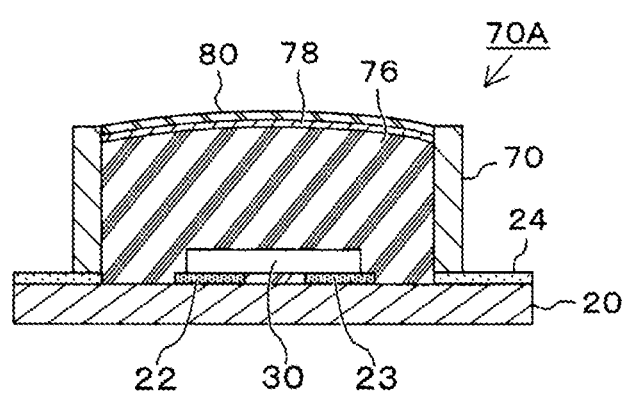
(C)

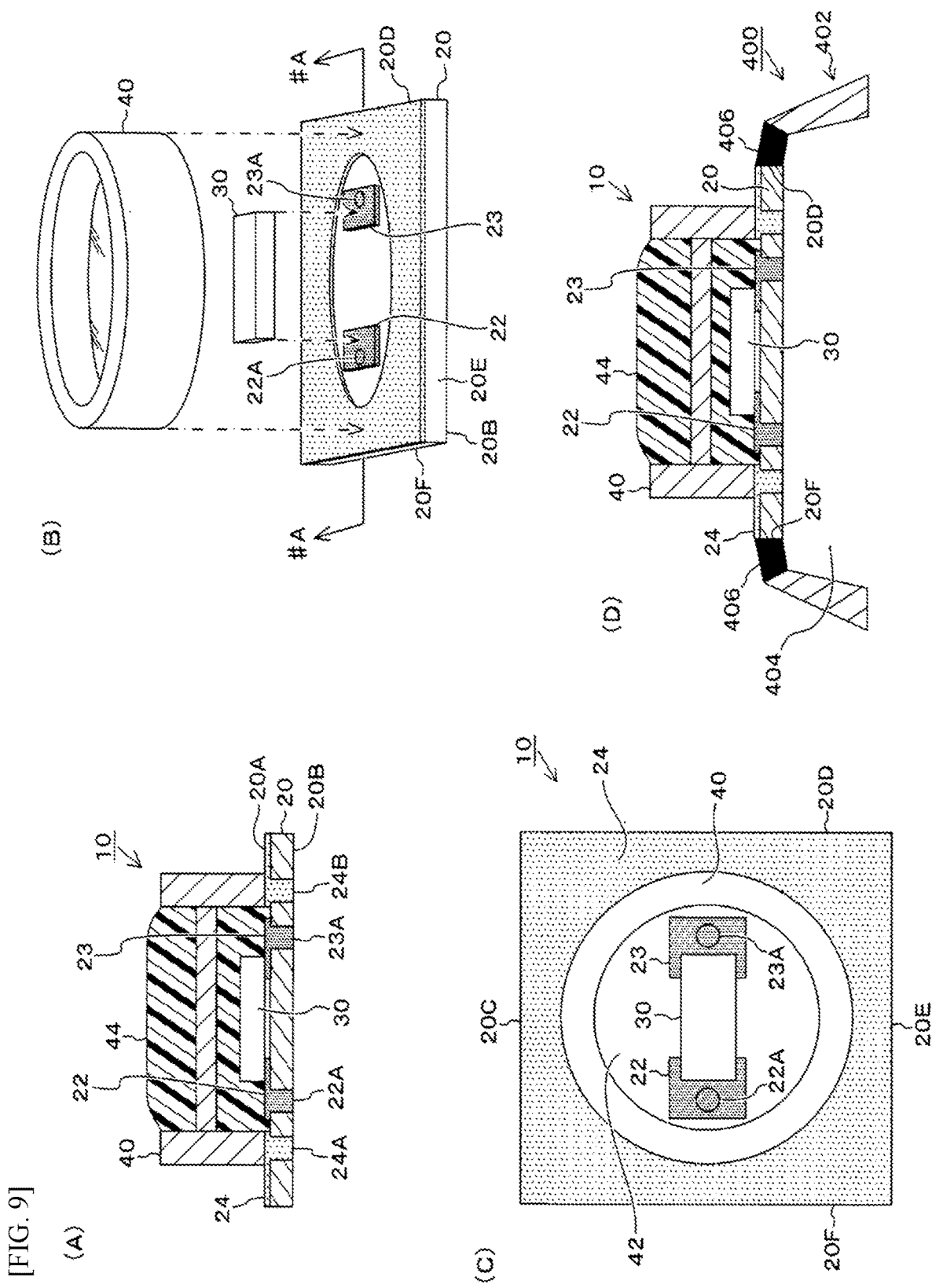

[FIG. 10]
(A)
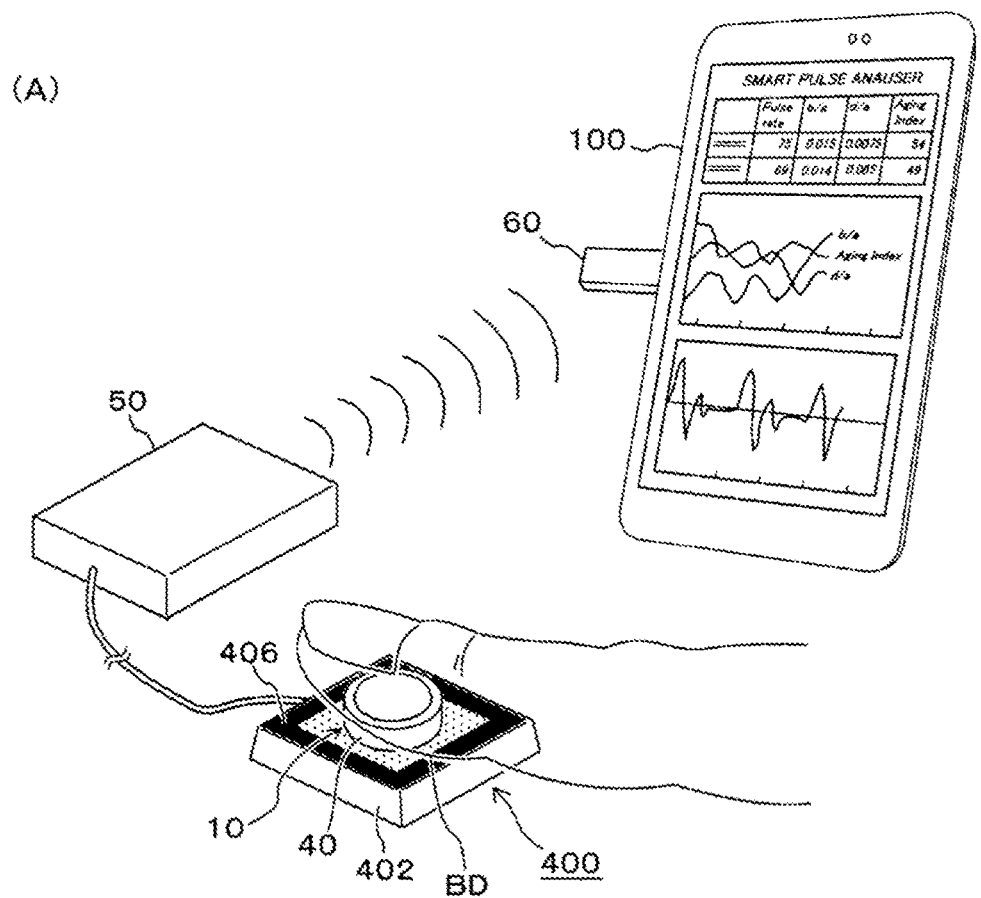
(B)
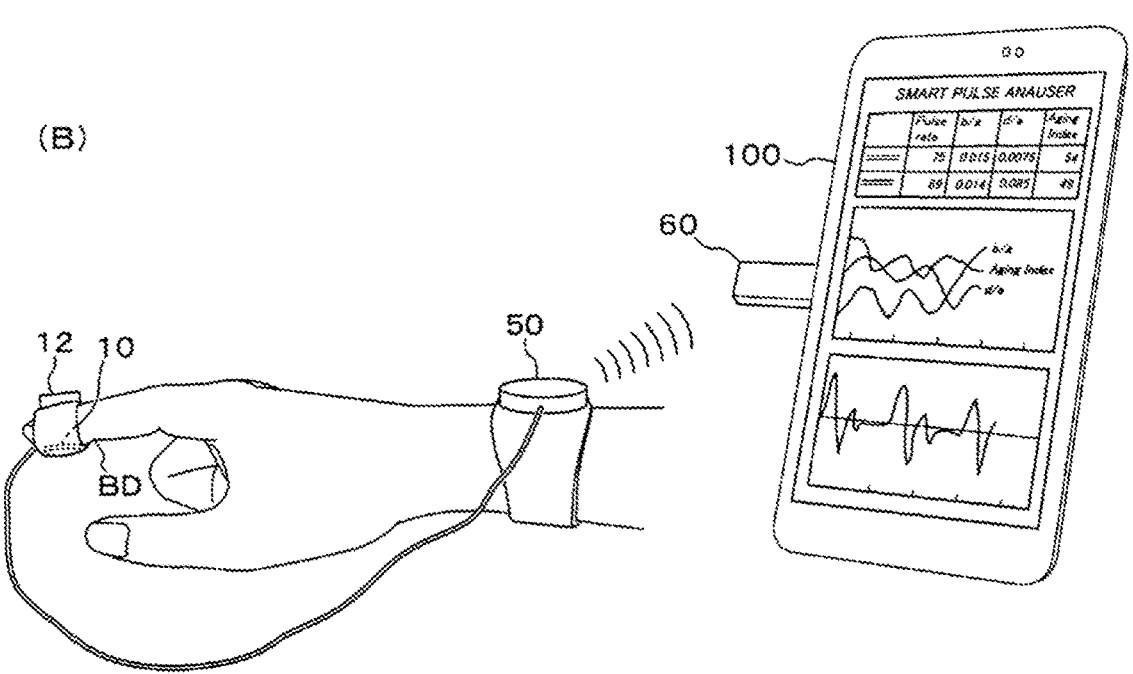

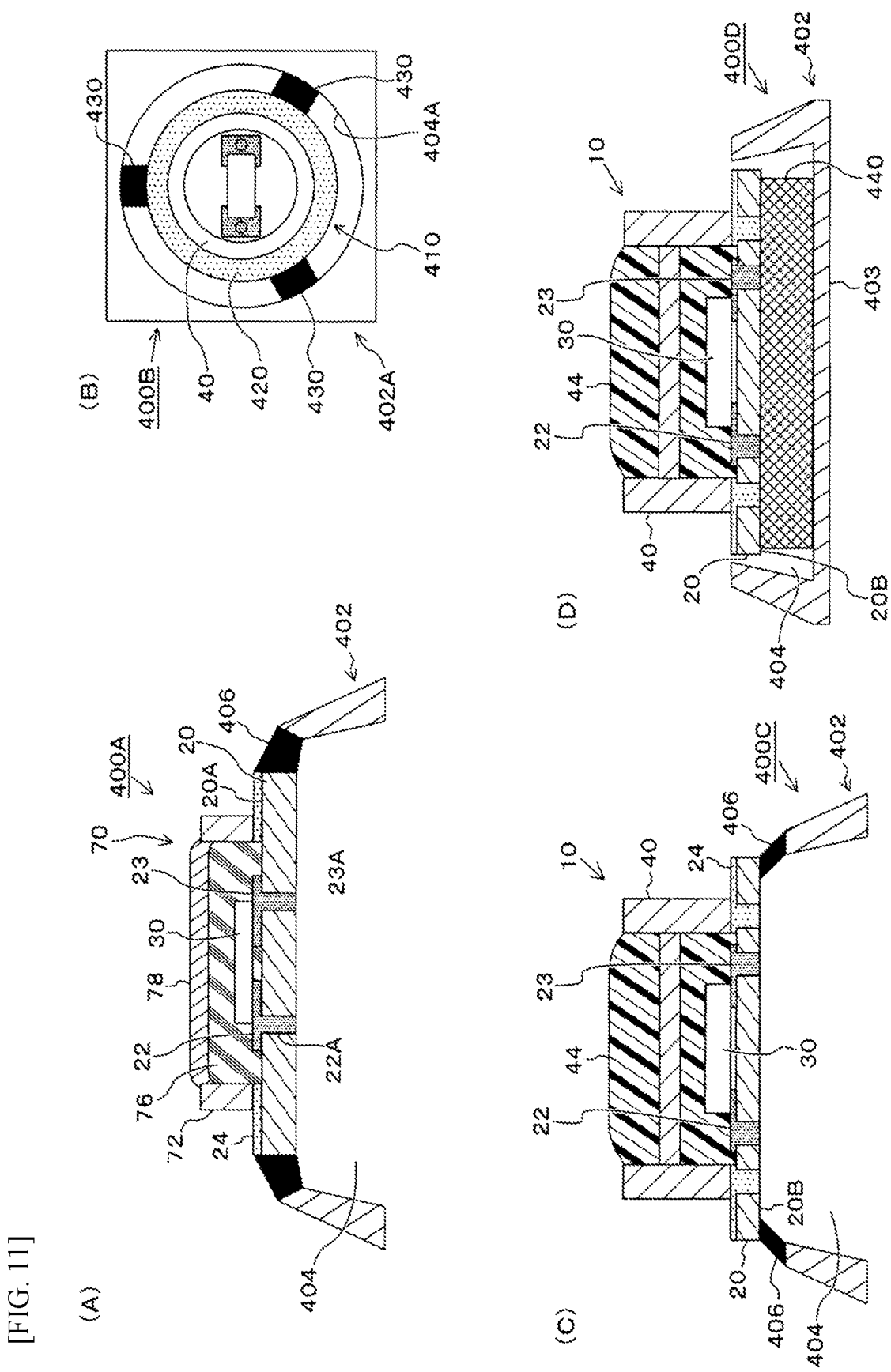
[FIG. 11]

VIBRATION WAVEFORM SENSOR AND PULSE WAVE DETECTION DEVICE

CROSS-REFERENCE TO RELATED APPLICATIONS

This application is the U.S. National Phase under 35 U.S.C. § 371 of International Application PCT/JP2017/004690, filed Feb. 9, 2017, which claims priority to Japanese Patent Applications No. 2016-090079, filed Apr. 28, 2016, No. 2016-159758, filed Aug. 16, 2016, and No. 2016-225514, filed Nov. 18, 2016. The International Application was published under PCT Article 21(2) in a language other than English.

TECHNICAL FIELD

The present invention relates to a vibration waveform sensor for measuring the waveforms of various vibrations such as pulses, as well as a pulse wave detection device using the same, and more specifically to a countermeasure to humming noise in sensors that utilize piezoelectric elements, as well as simplification of measurement using pulse wave detection devices.

BACKGROUND ART

Among the sensor devices with a catchphrase of helping the user manage his/her own health by continuously measuring the user's pulse waves, are so-called vibration waveform sensors that utilize piezoelectric elements. Vibration waveform sensors that utilize piezoelectric elements include, for example, the arteriosclerosis evaluation device described in Patent Literature 1 below. Patent Literature 1 discloses an arteriosclerosis evaluation device comprising: a first detection means for detecting a pulse wave transmitted through an artery in one location of a living body; a second detection means for measuring the blood flow rate in the artery of the living body; a first waveform specification means for specifying a first waveform based on the blood flow rate obtained by the second detection means; a second waveform determination means for obtaining a second waveform by subtracting the first waveform from the pulse wave detected by the first detection means; and an evaluation means for evaluating the degree of arteriosclerosis from the amplitude intensities of the first waveform and second waveform. It is disclosed that a piezoelectric transducer is used as the first detection means.

BACKGROUND ART LITERATURE

Patent Literature

Patent Literature 1: International Patent Laid-open No. 2010/024417

SUMMARY OF THE INVENTION

Problems to Be Solved by the Invention

However, while providing advantages such as the ease of finding pulse waves and the ability to obtain waveforms of high resolutions, any method using a piezoelectric element allows humming noise (noise arising from the frequencies of alternating-current power supplies) from power lines to be picked up easily, which presents a problem. Generation of such humming noise is inevitable so long as there are alternating-current power supplies nearby, and highly sensitive piezoelectric sensors are inescapably affected by humming noise.

Accordingly, conductive shields are used as a conventional countermeasure to prevent generation of humming noise. To be specific, this countermeasure involves attaching a conductive sheet around the sensor. However, this method does not provide a sufficient countermeasure to humming noise because it is structurally not possible to attach such sheet on the top face of the piezoelectric element. A conductive shield cannot be provided on the top face of the piezoelectric element, partly because this area must be coated with resin to maintain the moisture-proof and waterproof properties of the sensor or to spare the subject pain in his/her finger where this area comes in direct contact in order to capture pulse wave vibrations, and partly because the periphery of the piezoelectric element must be insulated to prevent short-circuiting. In other words, the conventional structure requires that the top face of the piezoelectric element is coated with insulating resin, which means that a conductive shield cannot be provided over this area.

On the other hand, detecting pulse wave vibrations from the arterial wall with a type of sensor that uses a piezoelectric element significantly limits the weight of the sensor module as a whole, because such weak vibrations must be discriminated from other noise, etc., for detection. To be specific, the weight of the entire module must be kept to approx. 5 g or less. In addition, the sensor must be taped around a fingertip or otherwise "being in a hanging down state" during measurement. Such mode of measurement makes the measurement process cumbersome, which adds to the difficulty of measurement.

The present invention focuses on the above points and one object is to, with respect to a highly sensitive vibration waveform sensor that uses a piezoelectric element, suppress the generation of humming noise in the sensor and make the sensor resistant to damage and thus more reliable.

Another object is to provide a pulse wave detection device capable of measuring pulse waves in a simpler manner, using the aforementioned vibration waveform sensor.

Means for Solving the Problems

The vibration waveform sensor proposed by the present invention is characterized in that it comprises: a board; a pair of conductive pads formed on the board; a pair of external conductors respectively led out from the pair of conductive pads; a piezoelectric element having a piezoelectric body and a pair of terminal electrodes formed on the piezoelectric body, where the pair of terminal electrodes are respectively connected to the pair of conductive pads and mounted on the board; and a conductive spacer formed, on the board, around the piezoelectric element and the pair of conductive pads, to a height greater than the mounted height of the piezoelectric element; wherein the spacer has a cover part, at a position lower than its rim part on the side opposite to the board, which continuously covers over the piezoelectric element and the pair of conductive pads.

A key embodiment is characterized in that the spacer has an H-shaped or M-shaped cross-section that crosses at right angles with the board. Another embodiment is characterized in that the spacer is formed in a manner surrounding the piezoelectric element and the pair of conductive pads. Yet another embodiment is characterized in that the spacer is like a frame or ring and has the cover part on the inner periphery face of the frame or ring. Or, it is characterized in that a silicone resin is filled in the area surrounded by the spacer.

Yet another embodiment is characterized in that the spacer comprises a pair of spacer members placed in a manner sandwiching the piezoelectric element and the pair of conductive pads, and the cover part provided across the pair of spacer members. Yet another embodiment is characterized in that a silicone resin is filled in the area sandwiched by the spacer. Yet another embodiment is characterized in that a conductive film is formed in areas on the board other than where the spacer and cover part are provided.

Another vibration waveform sensor proposed by the present invention is characterized in that it comprises: a board; a pair of conductive pads formed on the board; a pair of external conductors respectively led out from the pair of conductive pads; a piezoelectric element having a piezoelectric body and a pair of terminal electrodes formed on the piezoelectric body, where the pair of terminal electrodes are respectively connected to the pair of conductive pads and mounted on the board; a spacer formed, on the board, around the piezoelectric element and the pair of conductive pads, to a height greater than the mounted height of the piezoelectric element; an insulating resin formed on the board in a manner covering the piezoelectric element and the pair of conductive pads; and a conductive layer formed in a manner covering the insulating resin.

A key embodiment is characterized in that the spacer is formed in a manner surrounding the piezoelectric element and the pair of conductive pads. Another embodiment is characterized in that the spacer is like a frame or ring. Yet another embodiment is characterized in that the insulating resin and conductive layer are formed in the area surrounded by the spacer. Yet another embodiment is characterized in that a conductive film is formed in areas on the board other than where the spacer and insulating resin are provided.

Yet another embodiment is characterized in that the conductive layer is a resin that contains conductive grains. Yet another embodiment is characterized in that the exterior face of the spacer is formed by a conductor.

The pulse wave detection device proposed by the present invention is characterized in that it comprises: a vibration waveform sensor according to any of the foregoing; a housing having a receiving part on which the vibration waveform sensor is placed; and an elastic supporting means, provided between the vibration waveform sensor and the receiving part, for supporting the vibration waveform sensor on the receiving part of the housing.

A key embodiment is characterized in that the supporting means supports the vibration waveform sensor on the side faces of the board. Another embodiment is characterized in that the supporting means supports all around the side faces of the board. Yet another embodiment is characterized in that the supporting means supports the side faces of the board at multiple locations. The aforementioned and other objects, characteristics and benefits of the present invention shall be made clear by the detailed explanations below and the drawings attached hereto.

Effects of the Invention

According to the vibration waveform sensor proposed by the present invention, it comprises: a board; a pair of conductive pads formed on the board; a pair of external conductors respectively led out from the pair of conductive pads; a piezoelectric element having a piezoelectric body and a pair of terminal electrodes formed on the piezoelectric body, where the pair of terminal electrodes are respectively connected to the pair of conductive pads and mounted on the board; and a conductive spacer formed, on the board, around the piezoelectric element and the pair of conductive pads, to a height greater than the mounted height of the piezoelectric element; wherein the spacer has a cover part, at a position lower than its rim on the opposite side of the board, which continuously covers over the piezoelectric element and the pair of conductive pads. Accordingly, humming noise can be abated in a more dependable manner and the sensor becomes resistant to damage and thus more reliable.

According to another vibration waveform sensor proposed by the present invention, it comprises: a board; a pair of conductive pads formed on the board; a pair of external conductors respectively led out from the pair of conductive pads; a piezoelectric element having a piezoelectric body and a pair of terminal electrodes formed on the piezoelectric body, where the pair of terminal electrodes are respectively connected to the pair of conductive pads and mounted on the board; a spacer formed, on the board, around the piezoelectric element and the pair of conductive pads, to a height greater than the mounted height of the piezoelectric element; an insulating resin formed on the board in a manner covering the piezoelectric element and the pair of conductive pads; and a conductive layer formed in a manner covering the insulating resin. Accordingly, the conductive layer cuts off any humming noise from the top face of the piezoelectric element, while the circuit around the piezoelectric element is still insulated, which means that a vibration waveform sensor is obtained that can reduce humming noise without causing circuit failure (short-circuiting).

Additionally, according to the pulse wave detection device proposed by the present invention, the vibration waveform sensor according to any of the foregoing is supported in the receiving part of the housing by means of an elastic supporting means; what this means is that the person to be measured only needs to perform a simple operation of pressing his/her fingertip against the vibration waveform sensor to make the sensor contact the fingertip while being in a hanging down state, and this achieves an effect of making the detection of pulse waves easy.

BRIEF DESCRIPTION OF THE DRAWINGS

FIG. 1 Drawings showing the vibration waveform sensors in Example 1 of the present invention and an example of conventional art, where (A) is a cross-sectional view of Example 1, (B) is an assembly drawing for Example 1, (C) is a plan view showing Example 1 from the mounting-face side of the board, and (D) is a cross-sectional view of the vibration waveform sensor in the Comparative Example.

FIG. 2 Drawings showing the configuration of a system using the vibration waveform sensor in Example 1 above, where (A) shows the overall device configuration, while (B) and (C) are diagrams showing the circuit configurations.

FIG. 3 Drawings showing how a pulse moves and the skin vibrates.

FIG. 4 Drawings showing examples of humming noise in the vibration waveform sensor in the example of conventional art (shown in (A)) and vibration waveform sensor in Example 1 (shown in (B)).

FIG. 5 Drawings showing variation examples of Example 1 above, where (A) to (E) show other constitutional examples of vibration waveform sensors, while (F) shows an example of how a vibration waveform sensor is installed.

FIG. 6 Drawings showing the vibration waveform sensor in Example 2 of the present invention, where (A) is a cross-sectional view, (B) is an assembly drawing, and (C) is a plan view from the mounting-face side of the board.

FIG. 7 Drawings showing examples of humming noise in the vibration waveform sensor in the example of conventional art (shown in (A)) and vibration waveform sensor in Example 2 (shown in (B)).

FIG. 8 Drawings showing variation examples of Example 2 above.

FIG. 9 Drawings showing Example 3 of the present invention, where (A) is a cross-sectional view of the vibration waveform sensor (sensor module), (B) is an assembly drawing for the vibration waveform sensor, (C) is a plan view of the vibration waveform sensor from a principal-face side, and (D) is a cross-sectional view of the pulse wave detection device, which is a view, from the direction of the arrow, of a cross-section of (B) cut along line #A-#A.

FIG. 10 Drawings showing the overall configuration of the pulse wave detection device in Example 3 above and that of a conventional pulse wave detection device, where (A) shows the pulse wave detection device in Example 3, while (B) is a conventional pulse wave detection device.

FIG. 11 Drawings showing variation examples of Example 3 above.

MODE FOR CARRYING OUT THE INVENTION

The best modes for carrying out the present invention are explained in detail below based on examples.

Example 1

First, Example 1 of the present invention is explained by referring to FIGS. 1 to 4. In this example, the vibration waveform sensor proposed by the present invention is applied to a pulse wave sensor. FIGS. 1(A) to (C) are drawings showing this example, where (A) is a cross-sectional view, (B) is an exploded view, and (C) is a plan view from the mounting-face side of the board, of the vibration waveform sensor. FIG. 1(D) is a cross-sectional view of the vibration waveform sensor in an example of conventional art. FIG. 2 provides drawings showing the configuration of a system using the vibration waveform sensor in this example, where (A) is a drawing showing the overall device configuration, while (B) and (C) are drawings showing the circuit configuration. FIG. 3 provides drawings showing how a pulse moves and the skin vibrates. FIG. 4 provides drawings showing examples of humming noise in the vibration waveform sensor in the example of conventional art and vibration waveform sensor in this example. In these figures, the vibration waveform sensor 10 is constituted in such a way that a piezoelectric element 30 is placed on a principal face 20A of a board 20 and the periphery of this piezoelectric element 30 is covered with a spacer 40.

In this example, the spacer 40 is substantially ring-like, and has a ring part 42, and a cover part 44 which is substantially disk-like and provided roughly at the center of the ring part 42 in the height direction. In other words, the spacer 40 has a roughly H-shaped cross-section that crosses at right angles with the board 20, as shown in FIG. 1(A). In the illustrated example, the space surrounded by the board 20, ring part 42 and cover part 44 is filled with a silicone resin 46 in a manner covering the piezoelectric element 30. Additionally, the silicone resin 46 is also provided in the space formed by the rim part side of the ring part 42, and the cover part 44.

Among the aforementioned parts, the board 20 is used to securely support the piezoelectric element 30 and lead out its electrodes and amplify its signals, and is formed by glass epoxy, ceramic, etc. Dimension-wise, the board 20 is approx. 12 mm square in size and 1 mm in thickness, for example. On one principal face of the board 20, a pair of conductive pads 22, 23 are placed with an appropriate spacing in between near the center, and a conductive film 24 is formed around them. The piezoelectric element 30 is connected to both of the conductive pads 22, 23. The conductive pads 22, 23 are led out to the other principal face 20B of the board 20 via through holes 22A, 23A that penetrate the board 20 in its thickness direction, and are connected to a pair of external conductors (not illustrated). In the illustrated example, the piezoelectric element 30 is rectangular and has a piezoelectric body and a pair of terminal electrodes (not illustrated) formed on the piezoelectric body. Also, the pair of terminal electrodes are respectively joined to the pair of conductive pads 22, 23 by a solder, etc., and mounted on the one principal face 20A of the board 20.

As described above, the piezoelectric element 30 is connected to an amplifier (described below), etc., provided on the other principal face 20B side of the board 20, by the conductive pads 22, 23, through holes 22A, 23A and external conductors (not illustrated). For the piezoelectric element 30, PZT (lead zirconate titanate) is used, for example; however, its material is not limited in any way and any material having appropriate sensitivity (piezoelectric constant, capacitance) may be used. If the board 20 is 12 mm square in size, for example, the piezoelectric element 30 may be anything so long as its dimensions are approx. 0.6×0.3 mm to 3.2×1.6 mm.

Next, a ring-like spacer 40 is provided around the piezoelectric element 30 in a manner surrounding the piezoelectric element 30 and the pair of conductive pads 22, 23, where the spacer 40 is electrically joined to the conductive film 24. Also, the conductive film 24 is led out to the other principal face 20B side of the board 20 via through holes 24A, 24B. The spacer 40 is formed by stainless steel, for example, and conductive, creating a common ground potential between it and the human skin, etc., it contacts, and also functioning as a vibration introducer that introduces vibration from the skin, etc., and then introduces the vibration to the board 20.

The skin vibration is transmitted to the spacer 40 and also transmitted to the board 20 from the spacer 40. The board 20 also functions as a vibrator, so that the vibration transmitted from the spacer 40 is transmitted to the piezoelectric element 30. The material of the spacer 40 is not limited to a metal, and any material may be used so long as it is hard and conductive, such as a hard plastic whose surface is plated with a metal. Sandwiching such hard, conductive spacer 40 in between ensures transmission of pulse wave vibration and allows electrical noise to be released to the ground, and consequently pulse wave signals of higher definition can be obtained. This is the basic structure of the vibration waveform sensor, where a vibration pulse wave travels through the conductive spacer 40 and reaches the piezoelectric element 30 via the board 20, as illustrated schematically in FIG. 3. The piezoelectric element 30 detects this vibration, converts it to a voltage, and outputs the voltage to an analysis device, etc., as a pulse wave signal.

The basic structure of the vibration waveform sensor 10 is as described above; in this example, however, a highly insulating silicone resin 46 is filled between the piezoelectric body 30 and the cover part 44 of the spacer 40, and also between the edge part 42A side of the ring part 42 and the cover part 44, to deal with moisture in the air or sweat from the human body. Here, the silicone resin 46 may be filled by any amount so long as the edge part 42A is exposed. Needless to say, the silicone resin 46 is used because shorting must be prevented between the parts to be coated (piezoelectric element/conductive pads and spacer). Also, as shown in FIGS. 1(A) to (C), the conductive film 24 is provided to electromagnetically shield, and thereby protect from the effects of humming noise, the areas except where the ring part 42 and cover part 44 of the spacer 40 are provided, in order to suppress the generation of humming noise.

It should be noted that, although the silicone resin 46 may be filled by any amount on the edge part 42A side so long as the edge part 42A is exposed, preferably the silicone resin 46 is applied in the shape of a mound, as shown in FIG. 1(A), because doing so prevents the subject from feeling pain when wearing the sensor, while not affecting the acquisition of pulse waves.

The vibration waveform sensor 10 described above is worn on a human finger, etc., at an appropriate position using a medical fixing tape 12, etc., in such a way that the spacer 40 contacts the human skin BD, as shown in FIG. 2(A). It should be noted that the wear location of the vibration waveform sensor 10 may be an arm, and its wearing method may be wrapping it around the arm using a surface fastener.

Next, the basic operations of the vibration waveform sensor 10 are explained by referring to FIG. 3. FIGS. 3(A) to (C) show how a pulse wave is transmitted in a human blood vessel BV. A pulse wave is a change in blood volume resulting from an inflow of blood to a given part of an organ of the human body as the heart beats, which is captured from the body surface as a waveform. It should be noted that, in FIG. 3, the structure of the vibration waveform sensor 10 is simplified for better understanding. In FIG. 3, the parts of the blood vessel BV where the volume has increased are denoted by HP, indicating that a pulse wave is transmitting from left to right. The pulse wave reaches the spacer 40 of the vibration waveform sensor 10 via the skin BD. The vibration of the spacer 40 then vibrates the board 20, and this vibration is transmitted to the piezoelectric element 30. As a result, the piezoelectric element 30 displaces and the pulse wave vibration is converted to an electrical signal. This signal is amplified by an amplifier on the board 20 and output. It should be noted that the output waveform signal is primarily based on the displacement of the piezoelectric element 30 in the long-side direction (longitudinal direction). FIG. 4(B) shows an example of humming noise in the vibration waveform sensor in this example.

FIGS. 2(A) to (C) show an example of a waveform analysis system using the vibration waveform sensor 10 in this example. FIG. 2(A) shows the overall configuration, where the vibration waveform sensor 10 is connected to a mainboard 50, and the mainboard 50 is connected to a waveform analysis device 100 via a USB (Universal Serial Bus) dongle 60 for wireless communication.

FIG. 2(B) shows the circuit configuration of each part. The vibration waveform sensor 10 is such that the output side of the aforementioned piezoelectric element 30 is connected to the input side of an instrumentation amplifier (differential amplifier of high input impedance) 26 provided on the rear surface (principal face 20B) side of the board 20, and an output from this instrumentation amplifier 26 is connected to the input side of the mainboard 50 as an output from the vibration waveform sensor 10.

Provided on the input side of the mainboard 50 is a programmable amplifier 52 whose output side is connected to a transmitting module 54 via an A/D converter 53. In other words, the waveform signal of a pulse wave, which has been amplified by the programmable amplifier 52, is converted to a digital signal by the A/D converter 53 and transmitted from the transmitting module. For the transmitting module 54, a module conforming to any one of the various known standards for short-distance wireless communications using radio waves or infrared light, may be used. For example, BLE (Bluetooth® Low Energy) or other standard that provides for communications requiring low electric power may be utilized. Provided on the mainboard 50 is a button battery or other power supply 58, from which drive power is supplied to each part of the mainboard 50 and also to the vibration waveform sensor 10.

The USB dongle 60 allows the waveform analysis device 100 to load the signal transmitted from the mainboard 50, and comprises a receiving module 62 and a USB interface 64. It should be noted that the USB dongle 60 is not required so long as the signal transmitted from the mainboard 50 can be received directly by the waveform analysis device 100. The USB dongle 60 is also utilized for the operation control of the mainboard 50 by the waveform analysis device 100.

Next, the waveform analysis device 100 is constituted by a PC (personal computer), smartphone, tablet PC, etc., and comprises a CPU 102, a data memory 110, a program memory 120, and a display 104, as shown in FIG. 2(C). The program stored in the program memory 120 is run in the CPU 102. As the program runs, it references the data stored in the data memory 110. The calculational results are stored in the data memory 110, and also displayed on the display 104. These basic operations are general in nature and all in the public domain.

The data memory 110 stores the waveform data 112 received by the USB dongle 60. It also stores the calculation data 114, which represents the results of calculational operations by the CPU 102. The program memory 120 is provided with a noise elimination program 122, a waveform analysis program 124, an arrhythmia detection program 126, and an alert program 128. In the case of a smartphone, these programs are provided as apps.

Of these, the noise elimination program 122 is a program designed to eliminate the noise included in waveform data 112; when the peak value of a pulse wave exceeds a preset threshold, the program recognizes that a disturbance has occurred and holds the peak of the waveform, to perform signal processing that reduces the effect of disturbance. The waveform analysis program 124 calculates analysis values, such as Pb/Pa, Pc/Pa, Pd/Pa, Pe/Pa and (Pb-Pc-Pd-Pe)/Pa (Aging Index), for the Pa to Pe waves included in pulse waveforms. The arrythmia detection program 126 detects a missing pulse, as an occurrence of arrythmia, based on the pulse intervals of pulse waves. The alert program 128 outputs an alarm when the analysis result from the waveform analysis program 124 has exceeded a preset threshold, or the arrhythmia detection program 126 has detected arrythmia.

Calculating a first-order derivative of a pulse wave (velocity pulse wave) detected by the piezoelectric element 30 in this example gives an acceleration pulse wave, and a pulse waveform expressed along the vertical axis representing the amplitude of this acceleration pulse wave and the horizontal axis representing time, contains Pa to Pe waves. The waveform analysis program 124 performs the aforementioned first-order derivation and calculations based on the Pa to Pe waves. It should be noted that the meanings of the Pa to Pe waves are as follows:

Pa wave: Early systolic positive wave (Systolic anterior component of digital plethysmogram)

Pb wave: Early systolic negative wave (Same as above)
Pc wave: Midsystolic re-ascending wave (Systolic posterior component of digital plethysmogram)
Pd wave: Late systolic re-descending wave (Same as above)
Pe wave: Early diastolic positive wave (Diastolic component of digital plethysmogram)

Also, the waveform analysis program 124 calculates the average waveform of acceleration pulse waves and uses the wave height components of multiple waveforms contained in the acceleration pulse waves to calculate the wave height ratios Pb/Pa, Pc/Pa, Pd/Pa, Pe/Pa, (Pb-Pc-Pd-Pe)/Pa, etc. The meanings of the results of these calculations are described in the following literatures, for example:

a, Takazawa et al, "Assessment of Vasoactive Agents and Vascular Aging by the Second Derivative of Photoplethysmogram Waveform" Hypertension., August 1998 b, Junichiro Hashimoto et al, "Pulse wave velocity and the second derivative of the finger photoplethysmogram in treated hypertensive patients: their relationship and associating factors" Journal of Hypertension 2002, Vol 20 No 12

The arrythmia detection program 126 checks the pulse intervals and determines arrythmia has occurred when a pulse does not exist at a position where there should be a pulse. Also, the smartphone display shown in FIG. 2(A), or the display 104 of the waveform analysis device 100, displays, for example, the detected pulse waves, the results of analyzing the detected pulse waves in the waveform analysis device, and the like.

Next, the overall operations in this example are explained. A pulse wave signal output from the piezoelectric element 30 is amplified in the instrumentation amplifier 26, and then input to the mainboard 50. On the mainboard 50, the signal is further amplified in the programmable amplifier 52, and then converted to a digital signal in the A/D converter 53, after which the converted signal is transmitted from the transmitting module 54. The transmitted pulse wave signal is received by the receiving module 62 of the USB dongle 60, and input to the waveform analysis device 100 from the USB interface 64.

In the waveform analysis device 100, the input data is stored in the data memory 110 as waveform data 112. The noise elimination program 122 is run in the CPU 102, and if any disturbance exceeding a preset threshold is found in the waveform data 112, the peak of the waveform is held to eliminate the noise. The waveform analysis program 124 is run in the CPU 102, and Pa to Pe waves are detected from the waveform, while the aforementioned Pb/Pa, Pc/Pa, Pd/Pa, Pe/Pa, (Pb-Pc-Pd-Pe)/Pa, etc., are calculated, and the calculational results are stored in the data memory 110 as calculation data 114 and also displayed on the display 104. Also, the CPU 102 runs the arrythmia detection program 126 and detects arrythmia. Furthermore, if any of the aforementioned calculational results has exceeded a threshold or an occurrence of arrythmia has been detected, the alert program 128 outputs an optical or audible alarm.

FIG. 4 shows humming noise generated by a conventional vibration waveform sensor and this vibration waveform sensor according to the present invention. In FIG. 4, the horizontal axis represents time, while the vertical axis represents humming noise level (output voltage). The structure of the conventional sensor is as shown in FIG. 1(D). This vibration waveform sensor 10' has a structure where no cover part 44 is provided in the spacer 40, and humming noise in this conventional sensor is shown in FIG. 4(A). FIG. 4 (B) shows humming noise in the vibration waveform sensor in this example. When these humming noises are compared, it is clear that, with the vibration waveform sensor 10 in this example, the humming noise from the top face of the piezoelectric element 30 is effectively abated because the cover part 44 is provided on the interior side of the spacer 40 and the top face of the piezoelectric element 30 is covered with a continuous conductive surface.

As described above, the following effects are achieved in Example 1.

(1) A pair of conductive pads 22, 23 provided on a board 20, and a piezoelectric element 30 whose terminal electrodes are connected thereto, are surrounded by a conductive spacer 40, and a disk-like cover part 44 is provided on the interior side of the ring part 42 of the spacer 40 in a manner covering over the pair of conductive pads 22, 23 and the piezoelectric element 30. As a result, the cover part 44 abates the humming noise from the top face of the piezoelectric element 30 in a more dependable manner, while the circuit around the piezoelectric element 30 is insulated, and this reduces the humming noise without causing the circuit to fail (short). Also, parts of the board 20 except for the spacer 40 and cover part 44 are covered with a conductive film 24, which enables electromagnetic shielding in a more dependable manner.

(2) Because the spacer 40 is formed by a metal, electrical noise can be released to the ground and pulse wave signals of higher definition can be obtained as a result.

(3) Because a silicone resin 46 is filled in the area surrounded by the spacer 40, the piezoelectric element 30 can be protected, and also irritation that would otherwise be felt while the sensor is in use can be reduced. Also, the moisture-proof and water-proof properties of the sensor also improve. Furthermore, a pure silicone resin free from carbon or other powders may be used for the silicone resin 46, in which case the silicone resin area does not damage easily even when contacted many times by a finger, etc., which makes the sensor very reliable.

Variation Examples

Next, variation examples of this example are explained by referring to FIG. 5. In the aforementioned example, a silicone resin 46 was filled above and below the cover part 44 on the interior side of the spacer 40; however, this is only an example and filling of a silicone resin 46 in the space between the cover part 44 and the piezoelectric element 30 may be omitted, as is the case of the vibration waveform sensor 10A shown in FIG. 5(A). In addition, filling of a silicone resin 46 between the cover part 44 and the edge part 42A side of the ring part 42 may be omitted, as is the case of the vibration waveform sensor 10B shown in FIG. 5(B), or a silicone resin 46 may not be filled at all on the interior side of the spacer 40, as is the case of the vibration waveform sensor 10C shown in FIG. 5(C). In this example, the top face of the piezoelectric element 30 is shielded not only electromagnetically, but also physically, by the cover part 44, and this makes coating with a silicone resin no longer an absolute requirement. This means that, as to the question of which mode is to be used, an appropriate design should be determined as deemed appropriate according to the assumed use environment, etc. Furthermore, the cross-section need not have a perfect H shape; instead, the outer periphery side of the cover part 48 may be curved in a manner forming a depression that becomes deeper from the ring part 42 side toward the center, or specifically the cross-sectional shape may have an approximate M shape, as is the case of the vibration waveform sensor 10D shown in FIG. 5(D). In this case, too, the design can be changed as deemed appropriate and necessary based on whether or not to provide a silicone resin on both sides of the cover part 48.

Furthermore, while a ring-like spacer 40 was used in the aforementioned example, this is only an example and a spacer shaped like a square frame may be used; or, it may be a prism bonded only at two opposing sides, so long as the structure allows the spacer to make direct contact with the skin, etc. In the case of the vibration waveform sensor 200 shown in FIG. 5(E), a pair of sheet-like spacers 202, 204 are erected on the board 20 in a manner sandwiching the pair of conductive pads 22, 23 and piezoelectric element 30, and a rectangular cover part 206 is provided between them to cover over the piezoelectric element 30 and conductive pads 22, 23. In the illustrated example, a silicone resin 46 is filled between the piezoelectric element 30 and the cover part 206, and also between the cover part 206 and the edge part sides of the pair of spacers 202, 204; here, too, the decision on whether or not to fill a silicone resin may be changed as deemed appropriate and necessary, just like in the examples shown in FIGS. 5(A) to (C). The vibration waveform sensor 200 in this example also has an H-shaped cross-section, formed by the spacers 202, 204 and the cover part 206, which crosses at right angles with the board 20 and the pair of spacers 202, 204.

The vibration waveform sensor 220 in FIG. 5(F) represents an example where the sensor is provided in an electronic device such as smartphone or tablet PC. The vibration waveform sensor 220 is secured with a water-proof/dust-proof sealing material 234 in such a way that its ring-like spacer 232 on a board 230 is exposed from the housing 222 of the electronic device. The board 230 is vibratably supported with solder bumps 226 on the motherboard 224 of the electronic device. The vibration waveform signal from the vibration waveform sensor 220 is loaded into a circuit on the motherboard 224.

Example 2

Next, Example 2 of the present invention is explained by referring to FIGS. 6 and 7. In this example, too, the vibration waveform sensor proposed by the present invention is applied to a pulse wave sensor. FIG. 6 provides drawings illustrating this example, where (A) is a cross-sectional view, (B) is an exploded view, and (C) is a plan view from the mounting face side of the board, of the vibration waveform sensor. It should be noted that the same symbols are used for those constituents that are identical or corresponding to the equivalent constituents in Example 1 as described above (the same applies to the next example). FIG. 7 provides drawings showing examples of humming noise in the vibration waveform sensor in an example of conventional art and the vibration waveform sensor in this example. In these drawings, the vibration waveform sensor 70 is constituted in such a way that a piezoelectric element 30 is placed on a principal face 20A of a board 20, with the periphery of this piezoelectric element 30 covered with a spacer 72, and an insulating resin 76 and a conductive resin 78 are provided inside a cavity 74 formed on the interior side of the spacer 72.

Among the aforementioned parts, the board 20 is used to securely support the piezoelectric element 30 and lead out its electrodes and amplify its signals, and is formed by glass epoxy, ceramic, etc. Dimension-wise, the board 20 is approx. 12 mm square in size and 1 mm in thickness, for example. On one principal face of the board 20, a pair of conductive pads 22, 23 are placed with an appropriate spacing in between near the center, and a conductive film 24 is formed around them. The piezoelectric element 30 is connected to both of the conductive pads 22, 23. The conductive pads 22, 23 are led out to the other principal face 20B of the board 20 via through holes 22A, 23A that penetrate the board 20 in its thickness direction, and are connected to a pair of external conductors (not illustrated). In the illustrated example, the piezoelectric element 30 is rectangular and has a piezoelectric body and a pair of terminal electrodes (not illustrated) formed on the piezoelectric body. Also, the pair of terminal electrodes are respectively joined to the pair of conductive pads 22, 23 by a solder, etc., and mounted on the one principal face 20A of the board 20.

As described above, the piezoelectric element 30 is connected to an amplifier (described below), etc., provided on the other principal face 20B side of the board 20, by the conductive pads 22, 23, through holes 22A, 23A, and external conductors (not illustrated). For the piezoelectric element 30, PZT (lead zirconate titanate) is used, for example; however, its material is not limited in any way and any material having appropriate sensitivity (piezoelectric constant, capacitance) may be used. If the board 20 is 12 mm square in size, for example, the piezoelectric element 30 may be anything so long as its dimensions are approx. 0.6×0.3 mm to 3.2×1.6 mm.

Next, a ring-like spacer 72 is provided around the piezoelectric element 30 in a manner surrounding the piezoelectric element 30 and the pair of conductive pads 22, 23, where the spacer 72 is electrically joined to the conductive film 24. Also, the conductive film 24 is led out to the other principal face 20B side of the board 20 via through holes 24A, 24B (refer to FIG. 1(A)). The spacer 72 is formed by stainless steel, for example, and is conductive, creating a common ground potential between it and the human skin, etc., that it contacts, and also functioning as a vibration introducer that introduces vibration from the skin, etc., and then introduces the vibration to the board 20.

The skin vibration is transmitted to the spacer 72 and is also transmitted to the board 20 from the spacer 72. The board 20 also functions as a vibrator, so that the vibration transmitted from the spacer 72 is transmitted to the piezoelectric element 30. As shown in FIG. 6(C), a cavity 74 is formed by this spacer 72. The material of the spacer 72 is not limited to a metal, and any material may be used so long as it is hard and conductive, such as a hard plastic whose surface is plated with a metal. Sandwiching such hard, conductive spacer 72 in between ensures transmission of pulse wave vibration and allows electrical noise to be released to the ground, and consequently pulse wave signals of higher definition can be obtained. As shown in FIG. 3 in connection with Example 1 above, a vibration pulse wave travels through the conductive spacer 72 and reaches the piezoelectric element 30 via the board 20. The piezoelectric element 30 detects this vibration and converts it to a voltage, and outputs the voltage to an analysis device, etc., as a pulse wave signal.

The basic structure of the vibration waveform sensor 70 is as described above; however, a highly insulating resin 76 such as silicone is filled between the piezoelectric body 30 and the spacer 72, to deal with moisture in the air or sweat from the human body. Here, the insulating resin 76 may be filled by any amount so long as the edge part of the spacer 72 is exposed. For the insulating resin 76, normally silicone or other material offering high insulating property is used. Needless to say, this is because shorting must be prevented between the parts to be coated (piezoelectric element/conductive pads and spacer). Additionally, because this constitution is subject to the effects of humming noise, the conductive film 24 is provided, as shown in FIGS. 6(A) to (C), to create an electromagnetic shield and thereby suppress the generation of humming noise.

It should be noted that, under the present invention, the resin part inside the cavity 74 adopts a double-layer structure, as shown in FIG. 6(A), in order to suppress the generation of humming noise further. To be specific, a conductive resin 78 is provided over the insulating resin 76 under this structure. For the conductive resin 78, KE3494 manufactured by Shin-Etsu Silicone, or the like, is used, for example. KE3494 is a standard silicone in which conductive carbon is dispersed, and exhibits electrical conductivity once cured. It should be noted that the aforementioned product for conductive resin 78 is an example and any of various known materials may be used so long as it can form a soft conductive film. It should also be noted that, although the conductive resin 78 may be filled in the cavity 74 by any amount so long as the edge part of the spacer 72 is exposed, preferably the conductive resin 78 is applied over the insulating resin 76 in the shape of a mound, as shown in FIG. 6(A), because doing so prevents the subject from feeling pain when wearing the sensor, while not affecting the acquisition of pulse waves.

The vibration waveform sensor 70 described above is worn in the same manner as in Example 1 above, so that the spacer 72 contacts the human skin BD. The basic operations of the vibration waveform sensor 70 are as explained using FIGS. 3(A) to (C) in Example 1 above. The structure, circuit configurations, and overall operations of a waveform analysis system using the vibration waveform sensor 70 in this example are also the same as those in Example 1 as mentioned above.

FIG. 7 shows examples of humming noise in a conventional vibration waveform sensor and this vibration waveform sensor according to the present invention. In FIG. 7, the horizontal axis represents time, while the vertical axis represents humming noise level. The conventional sensor has the same structure as that of the vibration waveform sensor 70 shown in FIG. 6(A), except that the insulating resin 76 and conductive resin 78 have been removed, and humming noise in this conventional sensor is shown in FIG. 7(A). FIG. 7(B) shows humming noise in the vibration waveform sensor in this example. When these humming noises are compared, it is clear that, with the vibration waveform sensor 70 in this example, the humming noise from the top face of the piezoelectric element 30 is effectively cut off because the insulating resin 76 and conductive resin 78 are provided on the interior side of the spacer 72 to cover the top face of the piezoelectric element.

As described above, the following effects are achieved in Example 2.

(1) A pair of conductive pads 22, 23 provided on a board 20, and a piezoelectric element 30 whose terminal electrodes are connected thereto, are surrounded by a conductive spacer 72, while an insulating resin 76 is provided in a cavity 74 on the interior side of the spacer 72 in a manner covering the pair of conductive pads 22, 23 and the piezoelectric element 30, and furthermore a conductive resin 78 is provided in a manner covering the insulating resin 76. As a result, the conductive resin 78 abates the humming noise from the top face of the piezoelectric element 30, while the circuit around the piezoelectric element 30 is insulated, and this reduces the humming noise without causing the circuit to fail (short).

(2) Because the spacer 72 is formed by a metal, electrical noise can be released to the ground and pulse wave signals of higher definition can be obtained as a result.

Variation Examples

Next, variation examples of this example are explained by referring to FIG. 8. In the aforementioned embodiment shown in FIGS. 6 and 7, a ring-like spacer 72 was used; however, this is only an example and a spacer shaped like a square frame may be used; or, it may be a prism bonded only at two opposing sides, so long as the structure allows the spacer to make direct contact with the skin, etc. In the case of the vibration waveform sensor 300 shown in FIG. 8(A), a pair of sheet-like spacers 302, 304 are erected on the board 20 in a manner sandwiching the pair of conductive pads 22, 23 and piezoelectric element 30, and an insulating resin 76 and a conductive resin 78 are provided in between them to cover the pair of conductive pads 22, 23 and piezoelectric element 30. Also, as is the case of the vibration waveform sensor 310 shown in FIG. 8(B), the constitution may be such that a sheet-like or bar-like spacer 312 is erected on the board 20, while the piezoelectric element 30 is placed nearby, and the conductive pads 22, 23 and piezoelectric element 30 are covered with the insulating resin 76, and furthermore the insulating resin 76 is covered with the conductive resin 78. As described above, the spacer may have any shape so long as it can contact the target and allows its vibration to be transmitted to the board 20.

In the above example, the conductive pads 22, 23 and piezoelectric element 30 were covered with two layers of resin, namely, the insulating resin 76 and the conductive resin 78; however, as is the case of the vibration waveform sensor 70A shown in FIG. 8(C), for example, a three-layer structure may be adopted by providing a silicone or other insulating resin 80 in a manner covering the conductive resin 78 further. In this case, the conductive resin 78 is no longer contacted directly and thus it may contain metal grains without preventing the use of the sensor by persons allergic to metal. The vibration waveform sensor in this example may also be provided in an electronic device such as smartphone or tablet PC, as shown in FIG. 5(F) in connection with Example 1 above.

Example 3

Next, Example 3 of the present invention is explained by referring to FIGS. 9 and 10. FIG. 9(A) is a cross-sectional view of a vibration waveform sensor (sensor module), FIG. 9(B) is an assembly drawing for the vibration waveform sensor, FIG. 9(C) is a plan view of the vibration waveform sensor from a principal face side, and FIG. 9(D) is a cross-sectional view of a pulse wave detection device, which is a view, from the direction of the arrow, of a cross-section of (B) cut along line #A-#A. FIG. 10 provides drawings showing the overall configuration of the pulse wave detection device in Example 3 and that of a conventional pulse wave detection device, where (A) shows the pulse wave detection device in Example 3, while (B) shows the conventional pulse wave detection device.

In these figures, the vibration waveform sensor 10 in Example 1 above is used as the sensor module of the pulse wave detection device 400. The structure of the vibration waveform sensor 10 is the same as in Example 1 and therefore not explained. The vibration waveform sensor 10 as described above is traditionally worn on a human finger, etc., at an appropriate position using a medical fixing tape 12, etc., in such a way that the spacer 40 contacts the human skin BD at a fingertip, as shown in FIG. 10(B). Then, as shown in FIG. 10(B), measurements are taken with the sensor "in a hanging down state" (i.e., being worn on a finger cushion). However, this mode of measurement requires a cumbersome effort to wear the vibration waveform sensor 10 so that it is in a hanging down state, which prevents simple measurement of pulse waves. Also, even if a fingertip is pressed against the vibration waveform sensor 10 placed on a table, etc., pulse waves cannot be detected accurately because the vibration waveform sensor 10 picks up the vibrations of a heavier object (the table in this case).

Accordingly, under the present invention, the vibration waveform sensor 10 is installed on a receiving part 404 provided in the housing 402 of the pulse wave detection device 400, in a manner being suspended on an elastic supporting means 406, as shown in FIGS. 9(D) and 10(A). In this example, a supporting means 406 made of, for example, rubber, which is an elastic body, is joined, all around, to the side faces 20C to 20F of a square board 20 with an adhesive, and the supporting means 406 is further joined to the receiving part 404 of the housing 402 with an adhesive. The supporting means 406 is elastic and thus functions as a suspension member, which means that, even when the housing 402 is placed on a base and a fingertip is pressed against the vibration waveform sensor 10, pulse waves can be detected from the fingertip without the vibration waveform sensor 10 picking up the vibrations of the base.

In other words, as the person to be measured press his/her index finger strongly against this vibration waveform sensor 10 placed on the housing 402, the vibration waveform sensor 10 achieves sufficient adhesion force between it and the spacer 40 while still being in a hanging down state. The pulse waveforms obtained this way were equivalent to those obtained by the conventional measurement method shown in FIG. 10 (B). Any elastic member, in addition to rubber, can be used as the supporting means 406. Preferably the member has a spring rate of 0.5 to 7.0 N/mm; however, any other member whose spring rate is outside this range can be used as the supporting means under the present invention so long as it can achieve the same effects. For example, a sheet made of a material that itself is elastic may be used, or a metal spring, etc., that has been shaped to function as an elastic body can be used. The basic operations of the vibration waveform sensor 10 described above, and the overall configuration and circuit configuration of each part of a waveform analysis system that uses the pulse wave detection device 400, are the same as those described in Example 1 above.

Next, the overall operations in this example are explained. As the person to be measured presses his/her finger against the vibration waveform sensor 10 of the pulse wave detection device 400 installed on a base, as shown in FIG. 10(A), a pulse wave is transmitted to the piezoelectric element 30 via the spacer 40 and board 20. Here, since the vibration waveform sensor 10 is supported on the receiving part 404 of the housing 402 by the support 406 made of an elastic body, the vibration waveform sensor 10 detects the pulse wave transmitted from the fingertip pressed against it, without picking up the vibrations of the installation base, etc. The waveform analysis processing procedure that takes place after the transmitted vibration is output from the piezoelectric element 30 as a pulse wave signal, is the same as the procedure described in Example 1 above.

As described above, the following effects are achieved in Example 3.

(1) A vibration waveform sensor 10 comprising a board 20, a piezoelectric element 30, and a spacer 40, is supported, in a suspended manner, on a receiving part 404 of the housing 402 of a pulse wave detection device 400 via a supporting means 406 made of an elastic material. As a result, the person to be measured only needs to perform a simple operation of pressing his/her fingertip against the vibration waveform sensor 10 to make the sensor contact the fingertip while being in a hanging down state, and this achieves an effect of making the detection of pulse waves easy.

(2) Because the side faces of the board 20 are supported by the supporting means 406, the board 20 does not receive weight and thus the vibration waveform sensor 10 does not easily pick up vibrations from anything other than what is contacting it, which allows for detection of pulse waves in a dependable manner.

(3) Because the spacer 40 is formed by a metal, electrical noise can be released to the ground and pulse wave signals of higher definition can be obtained as a result.

Variation Examples

Next, variation examples of Example 3 are explained by referring to FIG. 11. Although the aforementioned embodiment used the vibration waveform sensor 10 in Example 1 as the sensor module, this is only an example and the vibration waveform sensor 70 in Example 2 may be utilized, as is the case of the pulse wave detection device 400A shown in FIG. 11(A). Also, while the supporting means 406 supports, all around, the side faces 20C to 20F of the board 20 in the examples shown in FIGS. 9 and 10, this is only an example and the design can be changed as deemed appropriate to the extent that the same effects are achieved. For example, the side rim part of a circular board 420 constituting a vibration waveform sensor 410 may be supported by a supporting means 430 at three points, as is the case of the pulse wave detection device 400B shown in FIG. 11(B). Also, the locations and number of supporting positions can be changed or increased/decreased as necessary to the extent that the same effects are achieved.

In addition, while the side faces of the board 20 of the vibration waveform sensor 10 were supported by the supporting means 406 in the above embodiment, this is only an example and the rim part of a principal face 20B of the board 20 may be supported by a supporting means 406, as is the case of the pulse wave detection device 400C shown in FIG. 11(C), or a supporting means 440 may be provided between a principal face 20B of the board 20 and the bottom face 403 of the housing 102 to support the vibration waveform sensor 10, as is the case of the pulse wave detection device 400D shown in FIG. 11(D).

It should be noted that the present invention is not limited to the aforementioned examples, and various changes may be added to the extent that the results do not deviate from the key points of the present invention. For example, the present invention includes the following:

(1) Although pulse waves were measured in Examples 1 and 2 above, the measuring target of the vibration waveform sensor proposed by the present invention is not limited to pulse waves, and breathing waveforms and various other known waveforms may be measured. For example, vibration waveforms of engines and motors may be analyzed.

(2) Although the vibration waveform sensor 10 and the mainboard 50 were provided as separate units in Example 1 above, the two may be provided as a single unit and even the waveform analysis device 100 may be constitutionally integrated therewith. Additionally, although a USB dongle was used to perform signal transmission based on BLE in the aforementioned example, such USB dongle is not required so long as the waveform analysis device has a function to send and receive signals to/from the mainboard. Also, the signal transmission standard is not limited to BLE, and any of various other standards may be applied.

(3) The calculational formulas for waveform analysis presented in the aforementioned example are also an example, and various calculations may be performed as necessary.

(4) Although a metal spacer 40 was used in Example 1 above, this is only an example, and the spacer may not be made of metal so long as it is hard and conductive. For example, it may be a resin, ceramic or other insulator body having a conductive film provided on its surface. The same applies to Examples 2 and 3.

(5) Although common PZT was used for the piezoelectric body in the aforementioned example, the piezoelectric body is not limited to PZT and any other material may be used so long as it has appropriate sensitivity (piezoelectric constant, capacitance) to achieve the same effects. Also, the shape and dimensions of the piezoelectric element 30 may be changed as deemed appropriate according to the application, etc.

(6) Although a glass epoxy resin was utilized for the board 20 in the aforementioned example, this is only an example and a ceramic or other harder material may be used.

(7) Although a silicone resin 46 was filled on the interior side of the ring-like spacer 40 in Example 1 above, its thickness can be changed as deemed appropriate and it may be provided in the form of a film.

(8) Although the conductive resin 78 used in Example 2 above was constituted by a silicone in which conductive carbon was dispersed, this is only an example and any of various other known conductive materials may be used so long as it is conductive and soft. It should be noted that, in consideration of metal allergy, etc., a material using non-metallic conductive carbon is preferred.

(9) Although the conductive resin 78 was filled on the interior side of the ring-like spacer 72 in Example 2 above, its thickness can be changed as deemed appropriate and it may be provided in the form of a film.

(10) The shapes, dimensions and materials shown in Example 3 are only examples and can be changed as deemed appropriate so long as the same effects are achieved. For example, the board 20, which was quadrilateral in the aforementioned example, may be circular.

(11) Although the mainboard 50 was provided on the exterior side of the housing 402 in Example 3 above, this is only an example and it may be provided inside the housing 402.

(12) Although the vibration waveform sensor (sensor module) was provided in an housing to be placed on a table in Example 3 above, this is only an example and the same effects can be achieved by, for example, providing the vibration waveform sensor, via an elastic supporting means, on a handle which is to be gripped by the person to be measured.

(13) Although rubber, which is an elastic material, was used for the supporting means 406 in Example 3 above, this is only an example and a metal spring, elastic sheet or other material may be used, in addition to rubber, so long as it has elasticity. For example, while a material having a spring rate in a range of 0.5 to 7.0 N/mm is preferred, but any other material whose spring rate is outside this range can be used as the supporting means under the present invention so long as it can achieve the same effects.

(14) Although the rubber supporting means 406 was bonded with an adhesive to the side faces 20C to 20F of the board 20 of the vibration waveform sensor 10 and also to the inner periphery of the receiving part 404 of the housing 402 in Example 3 above, this is only an example and any of various other known joining methods may be used, such as screws. It should be noted that an adhesive provides an excellent joining method from the viewpoint that the board 20 does not receive weight.

INDUSTRIAL FIELD OF APPLICATION

According to the present invention, it comprises: a board; a pair of conductive pads formed on the board; a pair of external conductors respectively led out from the pair of conductive pads; a piezoelectric element having a piezoelectric body and a pair of terminal electrodes formed on the piezoelectric body, where the pair of terminal electrodes are respectively connected to the pair of conductive pads and mounted on the board; and a conductive spacer formed, on the board, around the piezoelectric element and the pair of conductive pads, to a height greater than the mounted height of the piezoelectric element; wherein the spacer has a cover part, at a position lower than its rim part on the opposite side of the board, which continuously covers over the piezoelectric element and the pair of conductive pads. This way, humming noise can be cut off in a more dependable manner and the present invention becomes resistant to damage and thus more reliable, which makes the present invention suitable for vibration waveform sensor applications. In particular, it is ideal for pulse wave and other sensors that directly contact the skin.

According to another invention, the present invention comprises: a board; a pair of conductive pads formed on the board; a pair of external conductors respectively led out from the pair of conductive pads; a piezoelectric element having a piezoelectric body and a pair of terminal electrodes formed on the piezoelectric body, where the pair of terminal electrodes are respectively connected to the pair of conductive pads and mounted on the board; a spacer formed, on the board, around the piezoelectric element and the pair of conductive pads, to a height greater than the mounted height of the piezoelectric element; an insulating resin formed on the board in a manner covering the piezoelectric element and the pair of conductive pads; and a conductive layer formed in a manner covering the insulating resin.

Accordingly, the conductive layer cuts off any humming noise from the top face of the piezoelectric element, while the circuit around the piezoelectric element is still insulated, which means that humming noise can be reduced without causing circuit failure (short-circuiting), and therefore the present invention is suitable for vibration waveform applications. In particular, it is ideal for pulse wave and other sensors that directly contact the skin, because the resin-coated sensor does not inflict pain when contacted.

According to yet another invention, the present invention represents a vibration waveform sensor comprising a board, a piezoelectric element, and a vibration introducer, which is supported in a suspended manner on a receiving part of a housing via a supporting means formed by an elastic body; as a result, the person to be a subject only needs to perform a simple operation of pressing his/her fingertip against the sensor to make the sensor contact the fingertip while being in a hanging down state, which makes the present invention suitable for pulse wave measurement applications. In particular, it is ideal for stationary-type pulse wave detection devices and analysis systems.

DESCRIPTION OF THE SYMBOLS 10, 10', 10A to 10D: Vibration waveform sensor
12: Medical fixing tape
20: Board
20A, 20B: Principal face
20C to 20F: Side face
22, 23: Conductive pad
22A, 23A: Through hole
24: Conductive film
24A, 24B: Through hole
26: Instrumentation amplifier
30: Piezoelectric element
40: Spacer
42: Ring part
42A: Edge part
44, 48: Cover part
46: Silicone resin
50: Mainboard
52: Programmable amplifier
53: A/D converter
54: Transmitting module
58: Power supply
60: USB dongle
62: Receiving module
64: USB interface
70, 70A: Vibration waveform sensor
72: Spacer
74: Cavity
76, 80: Insulating resin
78: Conductive resin
100: Waveform analysis device
102: CPU
104: Display
110: Data memory
112: Waveform data
114: Calculational data
120: Program memory
122: Noise elimination program
124: Waveform analysis program
126: Arrythmia detection program
128: Alert program
200: Vibration waveform sensor
202, 204: Spacer
206: Cover part
220: Vibration waveform sensor
222: Housing
224: Motherboard
226: Solder bump
230: Board
232: Spacer
234: Water-proof/dust-proof sealing material
300: Vibration waveform sensor
302, 304: Spacer
310: Vibration waveform sensor
312: Spacer
400, 400A to 400D: Pulse wave detection device
402, 402A: Housing
403: Bottom face
404, 404A: Receiving part
406: Supporting means
410: Vibration waveform sensor
420: Board
430, 440: Supporting means BD: Skin
BV: Blood vessel
HP: Pulse wave

What is claimed is:

1. A vibration waveform sensor, characterized by comprising:
a board;
a pair of conductive pads formed on the board;
a pair of external conductors respectively led out from the pair of conductive pads;
a piezoelectric element having a piezoelectric body and a pair of terminal electrodes formed on the piezoelectric body, where the pair of terminal electrodes are respectively connected to the pair of conductive pads and mounted on the board; and
a conductive spacer formed, on the board, around the piezoelectric element and the pair of conductive pads, to a height greater than a mounted height of the piezoelectric element;
wherein the spacer includes a cover part and a rim part, wherein the cover part is at a position lower than the rim part on a side opposite to the board, wherein the cover part continuously covers an upper side of the piezoelectric element and an upper side of the pair of conductive pads in their entirety as viewed from above.

2. The vibration waveform sensor according to claim 1, characterized in that the spacer has an H-shaped or M-shaped cross-section that crosses at right angles with the board.

3. The vibration waveform sensor according to claim 1, characterized in that the spacer is formed in a manner surrounding the piezoelectric element and the pair of conductive pads.

4. The vibration waveform sensor according to claim 3, characterized in that the spacer is shaped in a frame or ring and has the cover part on an inner periphery face of the frame or ring.

5. The vibration waveform sensor according to claim 3, characterized in that a silicone resin is filled in an area surrounded by the spacer.

6. The vibration waveform sensor according to claim 1, characterized in that the spacer comprises a pair of spacer members placed in a manner sandwiching the piezoelectric element and the pair of conductive pads, and
the cover part is provided across the pair of spacer members.

7. The vibration waveform sensor according to claim 6, characterized in that a silicone resin is filled in an area sandwiched by the spacer.

8. The vibration waveform sensor according to claim 1, characterized in that a conductive film is formed in areas on the board other than where the spacer and cover part are provided.

9. A vibration waveform sensor, characterized by comprising:
a board;
a pair of conductive pads formed on the board;
a pair of external conductors respectively led out from the pair of conductive pads;
a piezoelectric element having a piezoelectric body and a pair of terminal electrodes formed on the piezoelectric body, where the pair of terminal electrodes are respectively connected to the pair of conductive pads and mounted on the board;

a spacer formed, on the board, around the piezoelectric element and the pair of conductive pads, to a height greater than a mounted height of the piezoelectric element;

an insulating resin formed on the board in a manner covering the piezoelectric element and the pair of conductive pads; and a conductive layer formed in a manner covering the insulating resin.

10. The vibration waveform sensor according to claim 9, characterized in that the spacer is formed in a manner surrounding the piezoelectric element and the pair of conductive pads.

11. The vibration waveform sensor according to claim 10, characterized in that the spacer is shaped in a frame or ring.

12. The vibration waveform sensor according to claim 10 characterized in that the insulating resin and the conductive layer are formed inside an area surrounded by the spacer.

13. The vibration waveform sensor according to claim 9, characterized in that the conductive film is formed in areas on the board other than where the spacer and the insulating resin are provided.

14. The vibration waveform sensor according to claim 9, characterized in that the conductive layer is a resin that contains conductive grains.

15. The vibration waveform sensor according to claim 1, characterized in that an exterior face of the spacer is formed by a conductor.

16. A pulse wave detection device, characterized by comprising:

the vibration waveform sensor according to claim 1;

a housing having a receiving part on which the vibration waveform sensor is placed; and an elastic supporting means, provided between the vibration waveform sensor and the receiving part, for supporting the vibration waveform sensor on the receiving part of the housing.

17. The pulse wave detection device according to claim 16, characterized in that the supporting means supports the vibration waveform sensor on side faces of the board.

18. The pulse wave detection device according to claim 17, characterized in that the supporting means supports all around the side faces of the board.

19. The pulse wave detection device according to claim 17, characterized in that the supporting means supports the side faces of the board at multiple locations.

* * * * *